(12) United States Patent
Qi

(10) Patent No.: US 9,719,983 B2
(45) Date of Patent: Aug. 1, 2017

(54) METHOD FOR STABILIZING QUANTUM-DOTS

(71) Applicant: FIO CORPORATION, Toronto (CA)

(72) Inventor: Bo Qi, Markham (CA)

(73) Assignee: FIO CORPORATION, Toronto (CA)

(*) Notice: Subject to any disclaimer, the term of this patent is extended or adjusted under 35 U.S.C. 154(b) by 144 days.

(21) Appl. No.: 14/397,314

(22) PCT Filed: Apr. 26, 2013

(86) PCT No.: PCT/CA2013/000421
§ 371 (c)(1),
(2) Date: Oct. 27, 2014

(87) PCT Pub. No.: WO2013/159211
PCT Pub. Date: Oct. 31, 2013

(65) Prior Publication Data
US 2015/0140678 A1    May 21, 2015

Related U.S. Application Data

(60) Provisional application No. 61/639,477, filed on Apr. 27, 2012.

(51) Int. Cl.
*G01N 33/52* (2006.01)
*G01N 21/64* (2006.01)
(Continued)

(52) U.S. Cl.
CPC ............ *G01N 33/525* (2013.01); *B82Y 30/00* (2013.01); *C09K 11/02* (2013.01); *G01N 21/6428* (2013.01); *Y10T 436/10* (2015.01)

(58) Field of Classification Search
CPC ........ B82Y 30/00; C09K 11/02; G01N 33/52; G01N 33/525; G01N 21/64; G01N 21/6428; Y10T 436/10; Y10T 436/109163; Y10T 436/21; Y10T 436/212; Y10T 436/25; Y10T 436/2525
(Continued)

(56) References Cited

U.S. PATENT DOCUMENTS

2003/0148544 A1    8/2003  Nie et al.
2006/0254315 A1   11/2006  Winkler et al.
(Continued)

FOREIGN PATENT DOCUMENTS

WO    WO 03003015    1/2003

OTHER PUBLICATIONS

Vassiltsova et al. Journal of Nanoscience and Nanotechnology, vol. 10, 2010, pp. 1635-1642.*
(Continued)

*Primary Examiner* — Maureen Wallenhorst
(74) *Attorney, Agent, or Firm* — DLA Piper LLP (US)

(57) ABSTRACT

A method for stabilizing quantum dots is disclosed, wherein the method includes the introduction of a first monomer into a miniemulsion system. In certain embodiments, the first monomer is a crosslinking polymer. In certain embodiments, a second monomer is added to the system to stabilize the quantum dots. In addition, a method of increasing the brightness of the quantum dots by adding a redox initiator system at a low temperature to reduce fluorescence quenching is also disclosed.

9 Claims, 29 Drawing Sheets

Introduction: Quantum dot (QD) here refers to Cadmium Selenide/Zinc Sulfide Quantum Dots CdSe/ZnS Core Shell Quantum Dot Organic surface ligand

(51) Int. Cl.
*C09K 11/02* (2006.01)
*B82Y 30/00* (2011.01)

(58) Field of Classification Search
USPC ..... 436/8, 19, 139, 140, 164, 166, 172, 174, 436/176
See application file for complete search history.

(56) References Cited

U.S. PATENT DOCUMENTS

2007/0161043 A1 7/2007 Nie et al.
2012/0256141 A1* 10/2012 Nick ........................ C08K 9/10
252/519.21

OTHER PUBLICATIONS

Ma et al. Journal of Materials Chemistry, vol. 21, 2011, pp. 13299-13305.*
Kohut-Svelko et al. Journal of Polymer Science: Part A: Polymer Chemistry, vol. 47, 2009, pp. 2917-2927.*
International Search Report from PCT/CA2013/000421 issued on Aug. 5, 2013.
International Preliminary Report on Patentability from PCT/CA2013/000421 issued on Sep. 4, 2014.

* cited by examiner

Second monomer
Lauryl acrylate
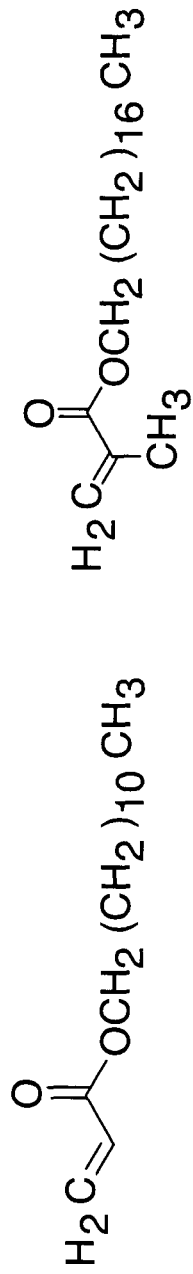
Stearyl methacrylate
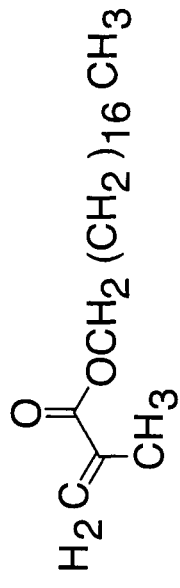
• Hexadecylamine
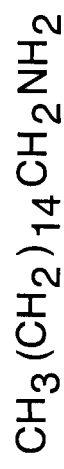
$CH_3(CH_2)_{14}CH_2NH_2$
FIG.3

Second monomer

| Monomer | Control | 3% | 5% | 10% |
|---|---|---|---|---|
| LA | M, H | M, H | M, H | P, L |
| SMA | | M H | P, L | P, L |

- M: monodisperse
- P: polydisperse
- H: high monomer conversion >90%
- L: low monomer conversion <90%

FIG.4

Second monomer: fluorescence intensity

| Barcode | Normalized intensity |
|---------|---------------------|
| Control | 1 |
| 3% LA | 1.4 |
| 5% LA | 1.6 |
| 3% SMA | 0.65 |

FIG.7

Redox initiator

| Initiator | Temperature °C | Monomer conversion % | Fluorescence intensity |
|---|---|---|---|
| KPS | 75 | 93 | 3.5 |
| KPS/NaHSO3 | 40 | 90 | 1 |
| CHPO/EDTA-Fe-CFS | 50 | 95 | quenched |
| APS/TMEDA | 40 | 13 | almost quenched |
| CHPO/TEDA | 50 | 5 | quenched |
| TBHP/EDTA-Fe-CFS | 50 | 20 | quenched |

FIG.13

Product requirements for QDBC

| Specifications | Required |
|---|---|
| concentration | TBD |
| size nm | 200-400 |
| polydispersity | <1.2 |
| excitiation wavelength nm | 400-480 |
| max emission wavelenth nm | 540-650 |
| half width at half maximum nm | <40 |
| surface functionality | TBD |
| Performance | |
| fluorescence efficiency | TBD |
| chemical stability | TBD |
| photo stability | TBD |
| thermo stability | TBD |
| Quality control | |
| raw material | TBD |
| manufacturing processes | TBD |
| post production characterization | TBD |
| batch to bach reproducibility | TBD |
| Cost | TBD |

FIG.19

Pros and Cons of QDs beads

| Comparation of QDBC and Dye fluorescence beads | | |
|---|---|---|
| Performance specificaitons | QDBC | Dye beads |
| excitation window | 2 | 3 |
| emision window | 2 | 4 |
| width of emissio spectum | 3 | 2 |
| fluorescence efficiency | 2 | 5 |
| stock shift | 3 | 3 |
| multiplex ability | 3 | 4 |
| Stability | | |
| chemical stability | 2 | 4 |
| photo stability | 3 | 3 |
| thermo stability | 2 | 5 |
| Manufacturing | | |
| raw material supplier (QD and dye) | 1 | 4 |
| production facility requirement | 2 | 4 |
| scalebility | 2 | 3 |
| cost | 2 | |
| Quality control | | |
| raw material (QD and dye) | 2 | 4 |
| manufacturing process | 2 | 4 |
| post production characterization | 2 | 2 |
| batch to batch reproducibility | 2 | 4 |
| Product maturity | 1 | 5 |

Note: top QDBC compares with top dye beads, score 5, means better more favorable for product, 1 is less favorable.

FIG.28

METHOD FOR STABILIZING QUANTUM-DOTS

CROSS REFERENCE TO RELATED APPLICATIONS

This application is a U.S. National Stage Application of International Application No. PCT/CA2013/000421 filed Apr. 26, 2013, which claims priority from U.S. Provisional Patent Application No. 61/639,477 filed Apr. 27, 2012. The entirety of all the above-listed applications are incorporated herein by reference.

TECHNICAL FIELD

The present relates generally to fluorescence detection and more particularly to an improved method for stabilizing Quantum-Dots.

BACKGROUND

Biomolecular assays may typically have required a readout signal to determine the success or failure of the experiment. Typically, for example, in prior art biomolecular sandwich assays, the analytes or target molecules to be detected may have been bound between biorecognition molecules (BRMs) and marker molecules. In the past, a positive result (and thus detection of the presence of the target molecule) may have been determined by detection of the readout signal, which in some cases may have been a fluorescent signal. The fluorescent signal may heretofore have been produced by excitation of a fluorophore bound to the marker molecule, such that the fluorophore emitted photons in the visible spectrum (i.e., as the fluorescent signal).

Exemplary prior art biomolecular sandwich assays may have included genomic assays, where the BRMs may have been single-stranded DNA immobilized on the surface of a substrate (e.g., a microbead). Similarly, the marker molecules may have included single-stranded marker DNA bound to one or more fluorophores. In operation, such prior art genomic assays may have involved a first hybridization reaction between the BRMs and the target molecules, if present. (The target molecules may have included single-stranded target DNA of interest in the experiment.) Thereafter, such prior art genomic assays may have involved a second hybridization reaction between the marker molecules and the target molecules, if present.

Other exemplary prior art biomolecular sandwich assays may have included immunoassays, where the BRMs may heretofore have been first antibody molecules immobilized on a substrate. Similarly, the marker molecules may heretofore have been second antibody molecules (alternately, "marker antibodies") bound to one or more fluorophores. In operation, such prior art immunoassays may have involved a first reaction between the BRMs and the target molecules, if present. (The target molecules may have included target antigen molecules, or analytes, of interest in the experiment.) Thereafter, such prior art immunoassays may have involved a second reaction between the marker antibodies and the target antigen molecules, if present.

In the past, it may generally have been thought that molecular fluorophores can provide useful and/or sensitive methods for the detection of binding events in biomolecular assays. Such molecular fluorophores may heretofore have been used, when bound, to provide a fluorescent readout signal. It may generally have been thought that suitable molecular fluorophores might include, for example, fluorescein, rhodamine dyes, or ALEXA FLUOR® series dyes (such as those manufactured by Molecular Probes, Inc. of Eugene, Oreg.). More recently, quantum dots (QDs) may have been considered for potential uses as fluorophores.

It may heretofore have been generally thought that assay sensitivity, and the ability to detect fluorescent readout signals, depends on an ability to observe an emission from a chosen marker fluorophore. Accordingly, much assay sensitivity research to date may have been largely aimed at increasing the ability to observe emissions from chosen marker fluorophores. Related developments may heretofore have, therefore, included highly sensitive photomultiplier tubes, more efficient photon collection optics, and/or the use of microfluidic systems. One or more of these developments may have sought to maximize detection sensitivity for very low fluxes of photons, possibly as might be emitted from a small area in a microarray or microbead biomolecular assay.

BRIEF SUMMARY

We have developed a method to improve the quantum dot stability through a synthetic process. Furthermore, we have improved the brightness, i.e. have reduced fluorescence quenching during synthesis using a redox initiator system (KPS/NaHSO$_3$ and APS/TMEDA) at lower temperature and have optimized the carboxylic surface function method. Also, we have developed a new bioconjugation strategy. The method is improved by introducing a crosslinking monomer, Divinylbenzene (DVB), into a miniemulsion system. A second monomer, such as Lauryl acrylate, stearyl methacrylate and the like is added also. This permits core-shell barcode beads synthesis and data analysis.

Accordingly in one aspect, there is provided a method for stabilizing quantum dots, the method comprising:
  introducing a first monomer into a miniemulsion system, the first monomer being a crosslinking polymer; and
  adding a second monomer to the system thereby stabilizing the quantum dots.

In one example, the crosslinking polymer is Divinylbenzene (DVB).

In one example, the second monomer is Lauryl acrylate or stearyl methacrylate.

In another example, the method further includes reducing fluorescence quenching by adding a redox initiator system at a low temperature so as to increase the brightness of the quantum dots.

In one example, the redox initiator system is KPS/NaHSO$_3$ and APS/TMEDA.

In one example, the low temperature is about 4° C.

Accordingly in another aspect, there is provided a method of increasing the brightness of quantum dots, the method comprising:
  adding a redox initiator system to a miniemulsion system, which includes a first monomer crosslinking polymer and a second monomer, at a low temperature to reduce fluorescence quenching, thereby increasing the brightness of the quantum dots.

BRIEF DESCRIPTION OF THE DRAWINGS

In order that the invention may be readily understood, embodiments of the invention are illustrated by way of example in the accompanying drawings.

FIG. 3 illustrated the chemical structures of second monomers lauryl acrylate (LA), stearyl methacrylate (SMA) and hexadecylamine;

FIG. 4 is a table showing dispersals of the second monomers;

FIG. 7 is a table illustrating the fluorescence intensity of the second monomer;

FIG. 13 is a table illustrating the effect of Redox initiator compounds on fluorescence intensity and monomer conversion;

FIG. 19 is a table illustrating the product requirements for QDBC;

FIG. 28 is a table showing the pros and cons of QD beads.

DETAILED DESCRIPTION

Figure 1:
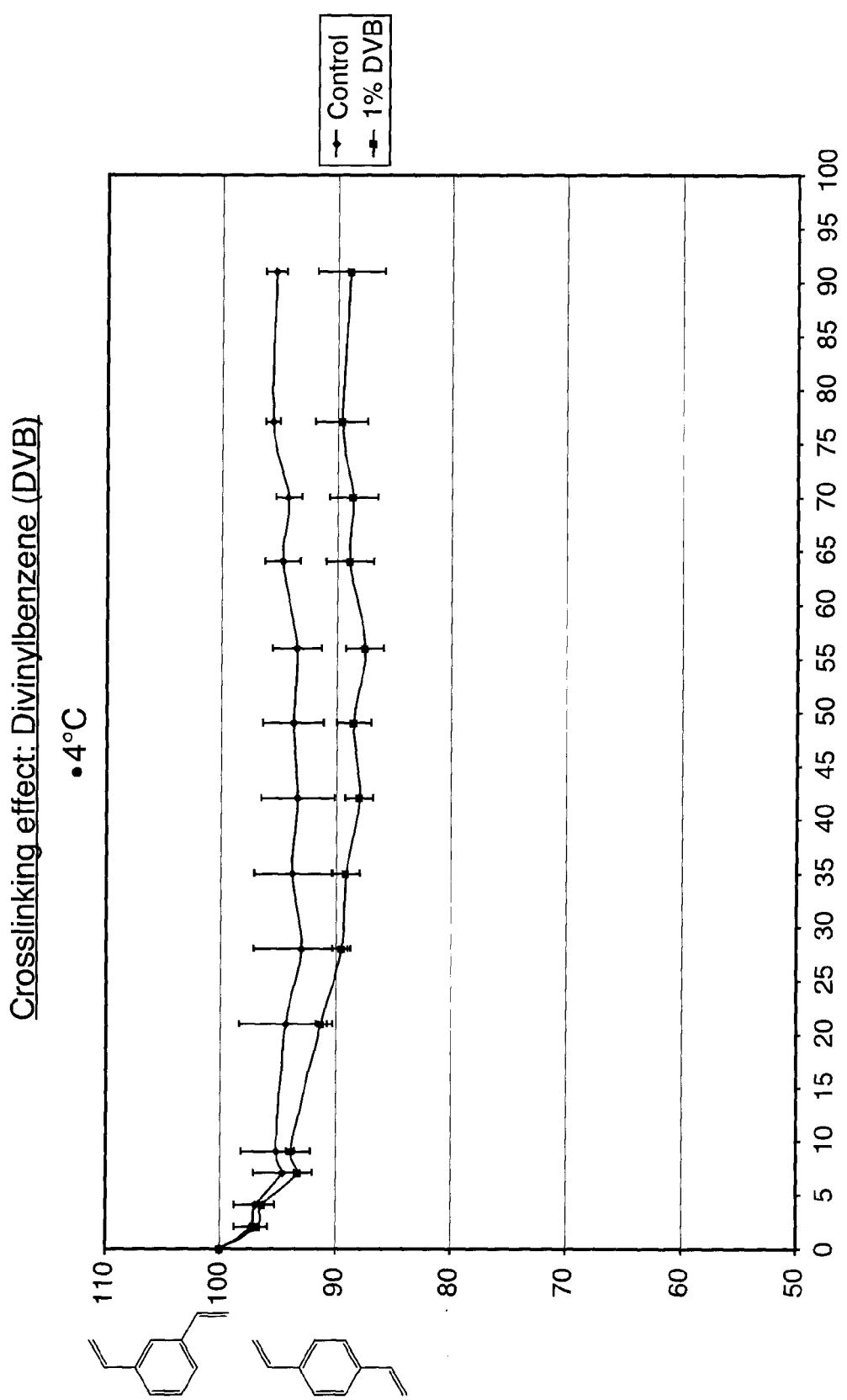
FIG. 1 is a graph illustrating the cross-linking effect of a first monomer Divinylbenzene (DVB) at 4° C.

In the following description of the embodiments, references to the accompanying drawings are by way of illustration of an example by which the invention may be practiced. It will be understood that other embodiments may be made without departing from the scope of the invention disclosed.

DEFINITIONS

Unless otherwise specified, the following definitions apply throughout:

As used herein, the singular forms "a", "an", and "the" include plural referents unless the context clearly indicates otherwise.

As used herein, the term "comprising" is intended to mean that the list of elements following the word "comprising" are required or mandatory but that other elements are optional and may or may not be present.

As used herein, the term "consisting of" is intended to mean including and limited to whatever follows the phrase "consisting of". Thus the phrase "consisting of" indicates that the listed elements are required or mandatory and that no other elements may be present.

We prepared quantum dot barcode microbeads using a miniemulsion polymerization processes. There are two major challenges to produce barcode microbeads with controllable size, higher brightness and better performance on LF stripe (surface function, low non-specific binding and higher environment stability). In order to achieve this, we have optimized the miniemulsion polymerization process by improving the stability through optimization of synthesis process and by improving the brightness by a redox initiator system.

1. Crosslinking on Stability of QD Barcode Beads

We introduced a monomer, Divinylbenzene (DVB), into polystyrene miniemulsion polymerization, to investigate the effect of crosslinking monomer on stability of polymerization process and QD barcode beads stability.

We used miniemulsion polymerization without quantum dot, but with DVB at 0.2%, 0.5%, 1%, 2%, 5% wt % to styrene concentration.

We characterized the beads by size, CV, emulsion stability (by measuring the gel portion after polymerization)

We selected the appropriate DVB monomer usage (Low CV, stable emulsion process) to conduct quantum dot barcode beads synthesis.

We characterized the quantum dot barcode beads (size, CV,) using an Agilent particle sizer.

2. Addition of a Second Monomer such as Lauryol Acrylate (LA) or Stearyl Methacrylate (SMA)

For the miniemulsion polymerization of styrene we used two different second monomers at different amounts (0.3%, 5%, 10%, 15%, 20%)

We characterized the copolymer by NMR, FTIR and DSC to confirm the copolymer composition and property.

We conducted the quantum dot barcode beads synthesis with the second monomer by miniemulsion polymerization (with different amount of the second monomer).

3. Core-Shell Barcode Synthesis

We used an emulsion polymerization of seed polystyrene beads.

We used shell-adding to seed polystyrene beads with styrene.

We compared the seed and core-shell bead sizes to confirm the shell-adding process.

We used the core-shell process to synthesis quantum dot core beads with polystyrene or PMMA shell.

We used surface function of quantum dot barcode seed beads and quantum dot core-shell beads to evaluate the quenching effect.

4. Stability Study for Crosslinking, Second Monomer, and Core-Shell QD Barcode Beads We determined the stability by dispensing QD barcode beads onto nitrocellulose membrane in 96 clear bottom black wall plate, read by M2e plate reader storage at about 4° C. in refrigerator and about 45° C. in oven.

5. Effect of Redox Initiator on Brightness of QD Barcode Beads

We used polystyrene miniemulsion polymerization by redox initiator system (KPS/NaHSO$_3$ and APS/TMEDA.) and regular KPS system. (APS=ammonium persulfate; TMEDA=tetramethyl ethylene diamine).

We evaluated the two processes by beads size, CV, and monomer conversion.

We evaluated quantum dot barcode beads with redox initiator system.

We compared the quench effect with thermal initiator (KPS) and redox initiator system Brightness was determined from sample intensity read by M2e plate reader, the QD barcode beads sample is dispensed in 96 clear bottom black wall plate with a nitrocellulose.

6. Sample Rating Rationale

Sample rating was based on average % fluorescence emission and corresponding coefficient of variation (CV) reflecting sample behavior over a certain number of testing days.

Figure 2:
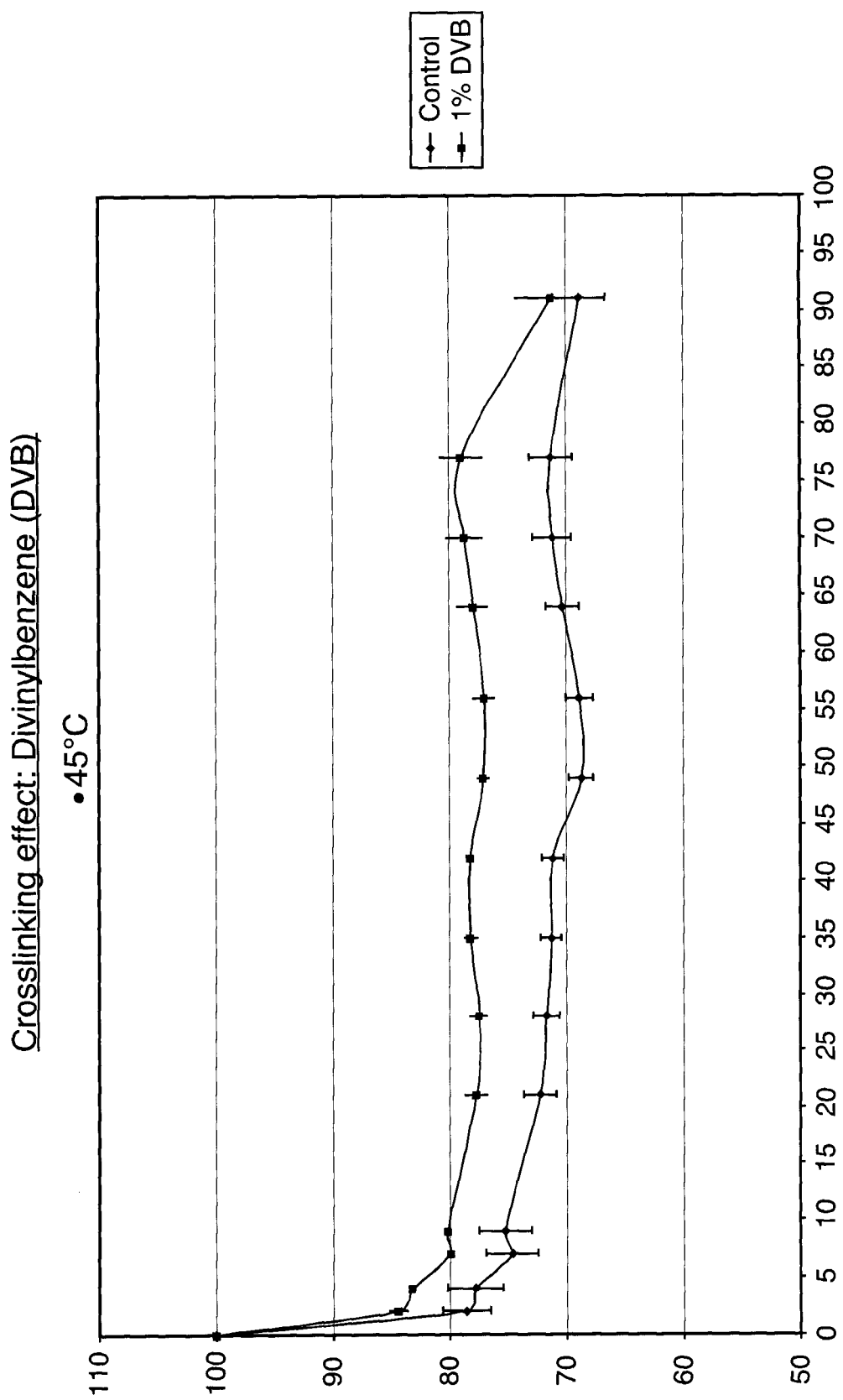
FIG. 2 is a is a graph illustrating the cross-linking effect of the Divinylbenzene (DVB) at 45° C.

Each sample received a rating comprised of 2 digits separated by a decimal point. The first & second number represents the CV and average % fluorescence emission category rating respectively. CV value takes precedence over average % fluorescence emission value for sample rating, because CV value readily reflects the range of fluctuation in a sample's day-to-day % fluorescence emission, thus this number is directly related to sample stability. Calculations were done with reference from Day Results 1. Crosslinking Monomer We have found that polystyrene beads become polydispersed after miniemulsion polymerization with increase of amount of crosslinking monomer DVB over 1 Wt % to styrene. Therefore, the polystyrene QD barcode beads for crosslinking study was synthesized with 1% DVB. FIG. 1 illustrates QD barcode beads fluorescence intensity with time at about 4° C. (the control means without DVB). Referring to FIG. 2, the QD barcode beads fluorescence intensity is illustrated over time at about 45° C. (where control means without DVB).

2. Second Monomer

Referring to the table in FIG. 4, there is illustrated polystyrene beads after miniemulsion polymerization with different amounts of second monomer. In the table, the following legend applies: M: monodisperse, P: polydisperse, H: high monomer conversion. >90%, L: low monomer concersion <90%

Figure 5:
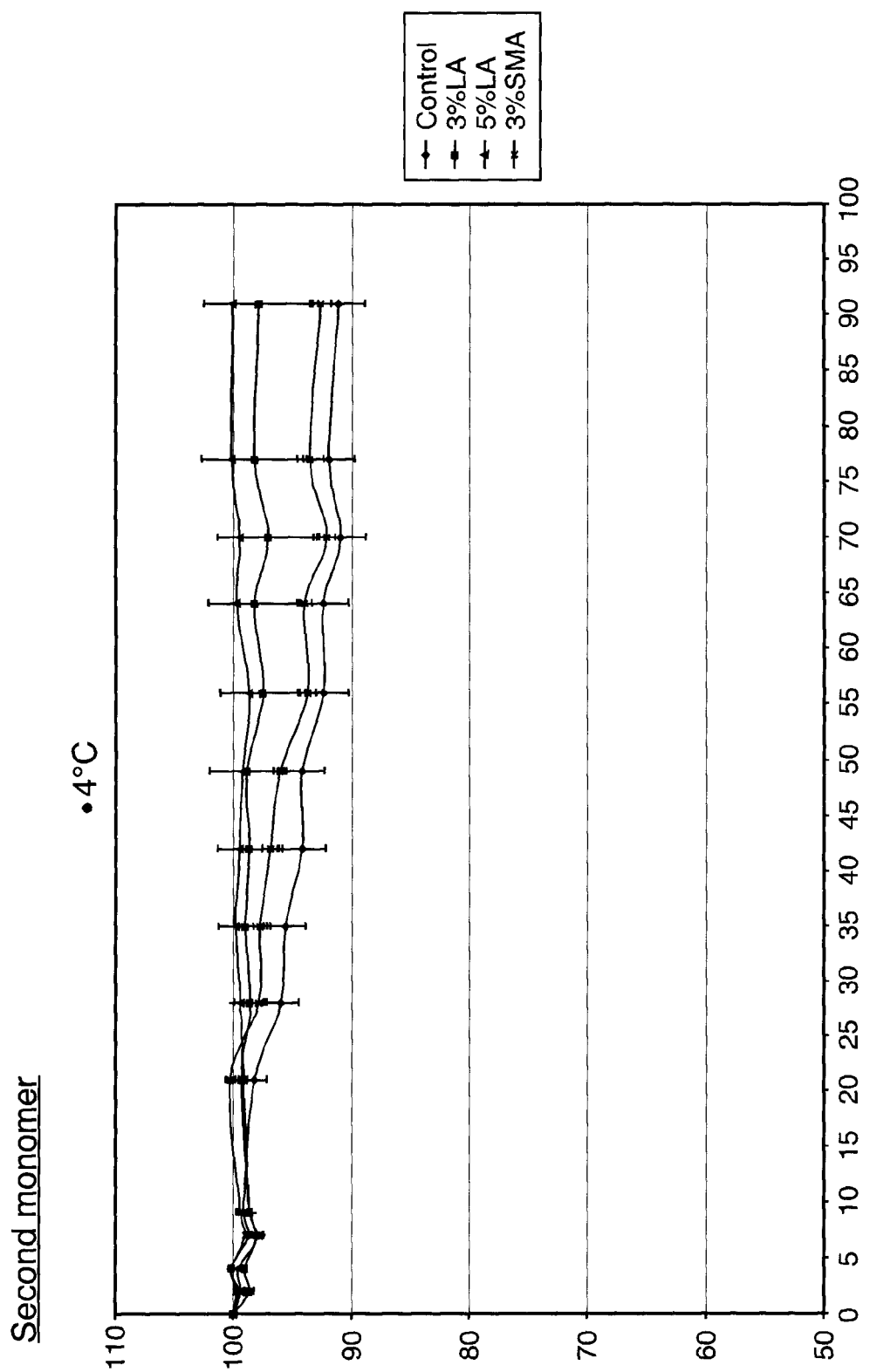
FIG. 5 is a graph showing the second monomer at 4° C.
Figure 6:
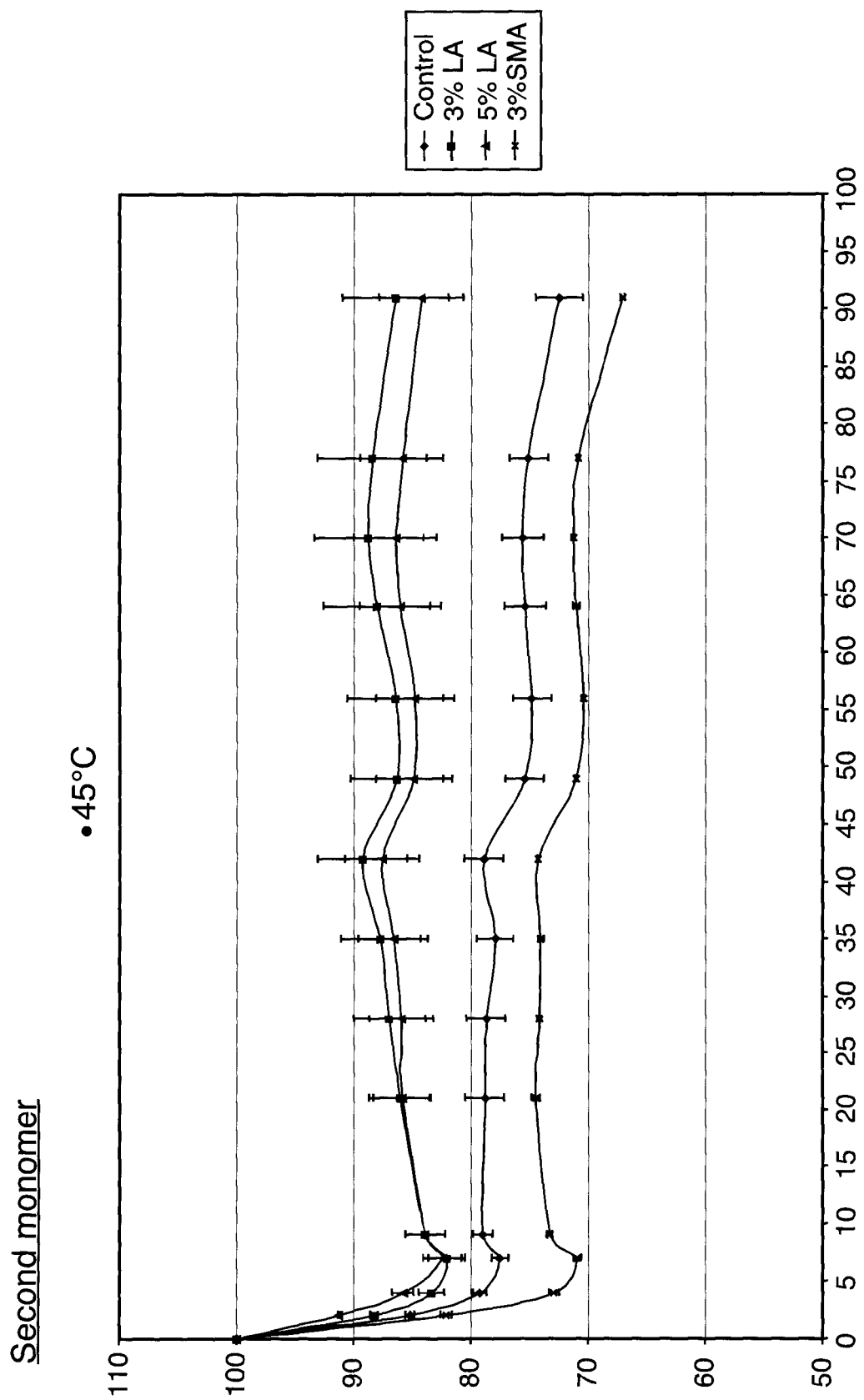
FIG. 6 is a graph showing the second monomer at 45° C.

Adding the second monomer affects the performance of miniemulsion polymerization. Referring to FIGS. 5 and 6, the data shows that when the amount of the second monomer increases, the monomer conversion decreases and beads become polydisperse. For QD barcode beads synthesis, 3%, 5% LA and 3% SMA were added as second monomer.

Referring to FIG. 7, the Table illustrates the intensity of QD barcode beads with a second monomer where the data is from a sample stored at about 45° C. at day 91.

3. Core-Shell Barcode Synthesis

Figure 8:
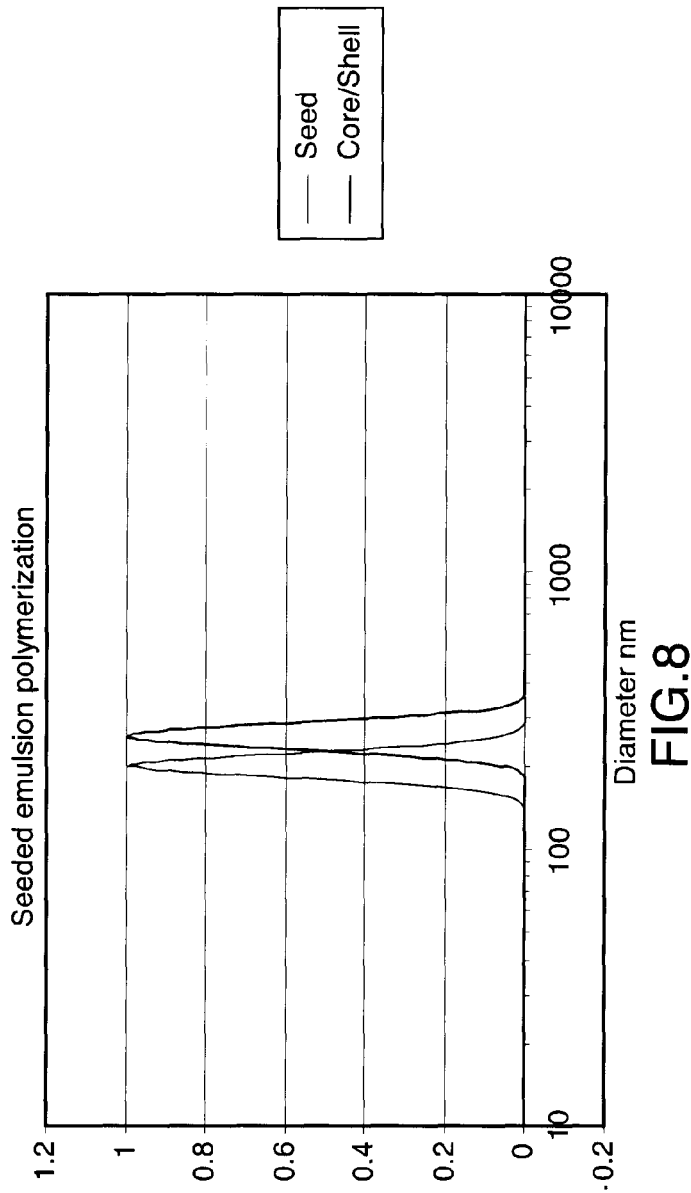
FIG. 8 illustrates data from core-shell barcode beads.
Figure 9:
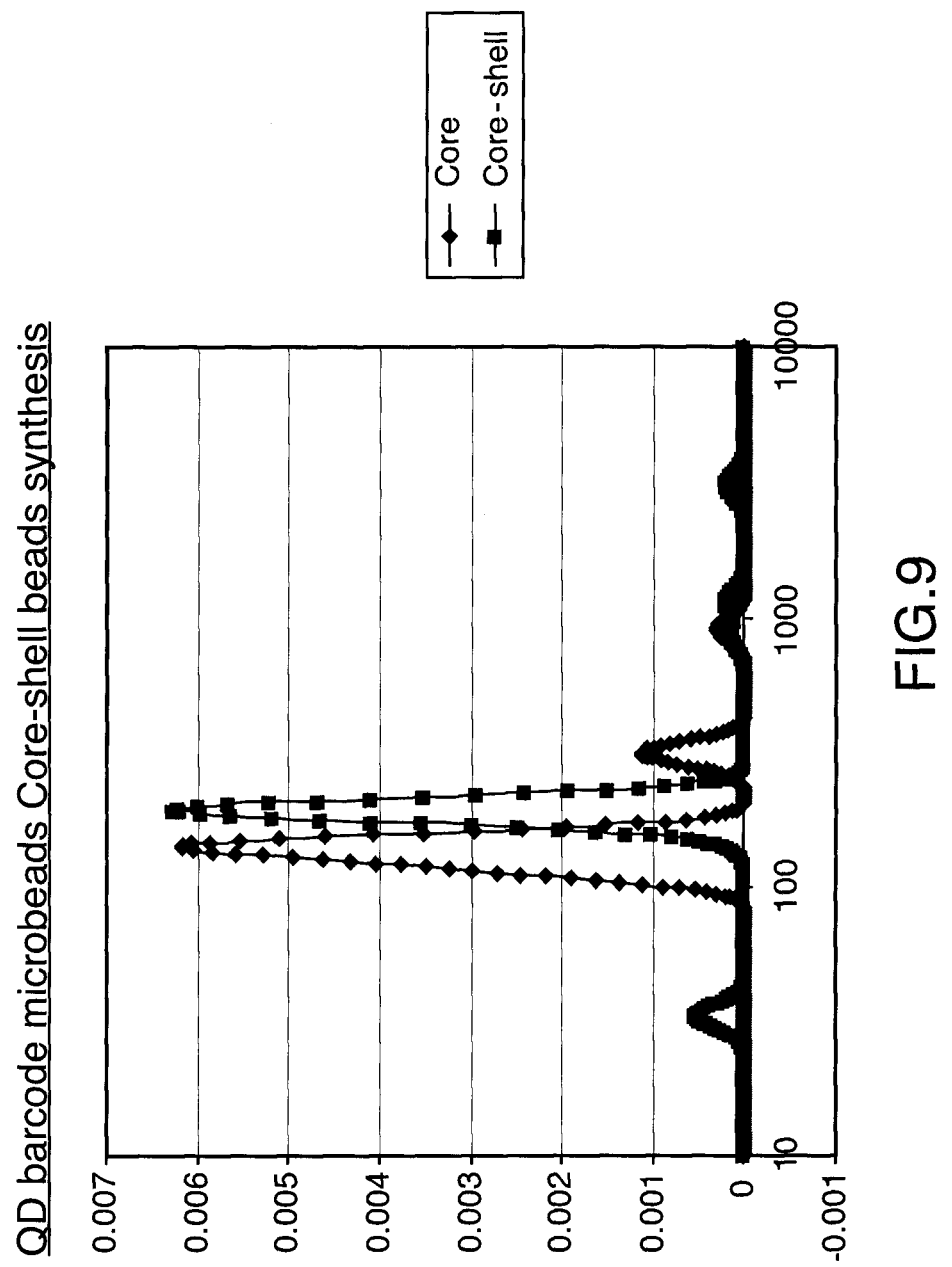
FIG. 9 illustrates QD barcode microbeads: Core-shell beads synthesis.
Figure 10:
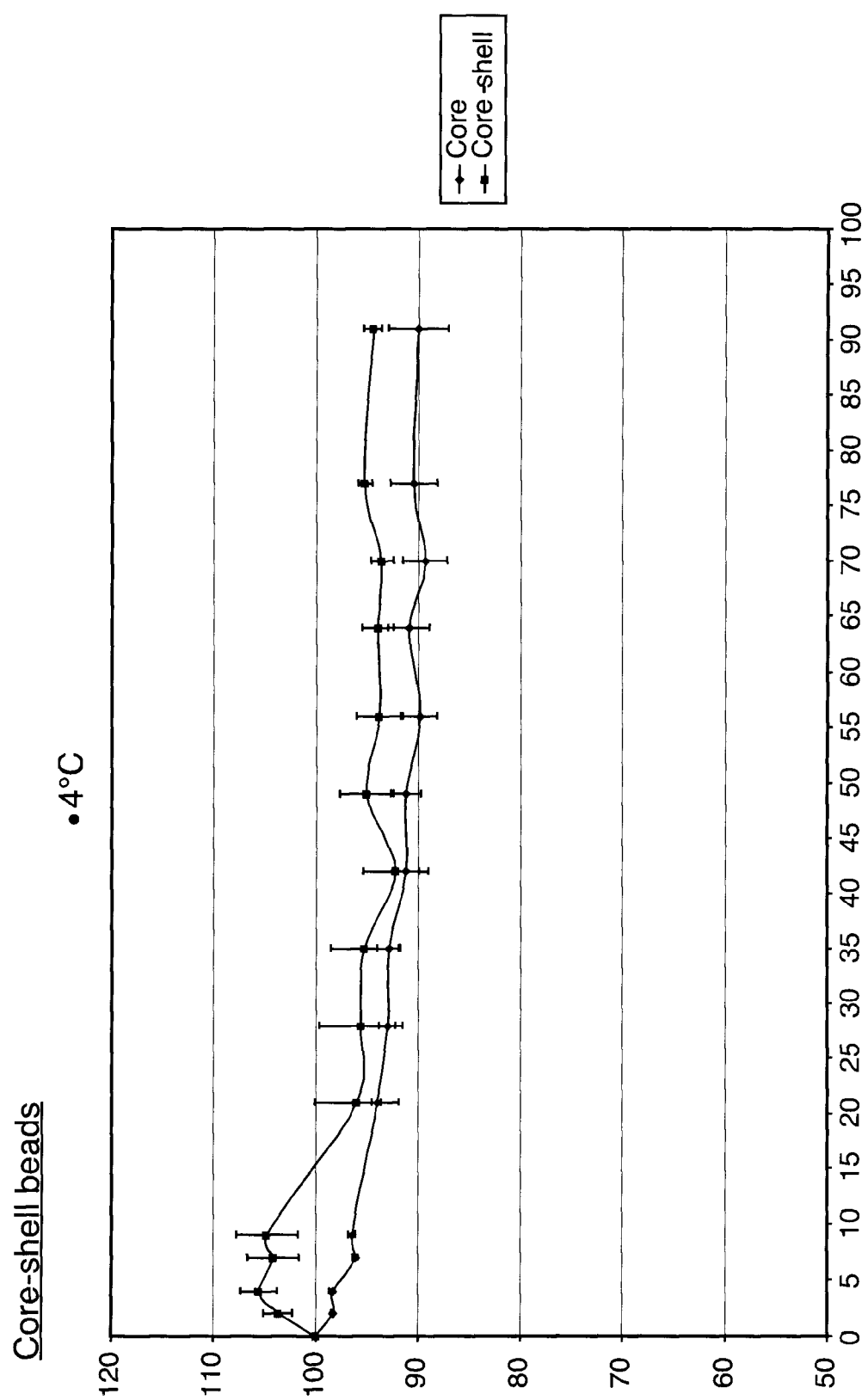
FIG. 10 is a graph showing core-shell beads at 4° C.
Figure 11:
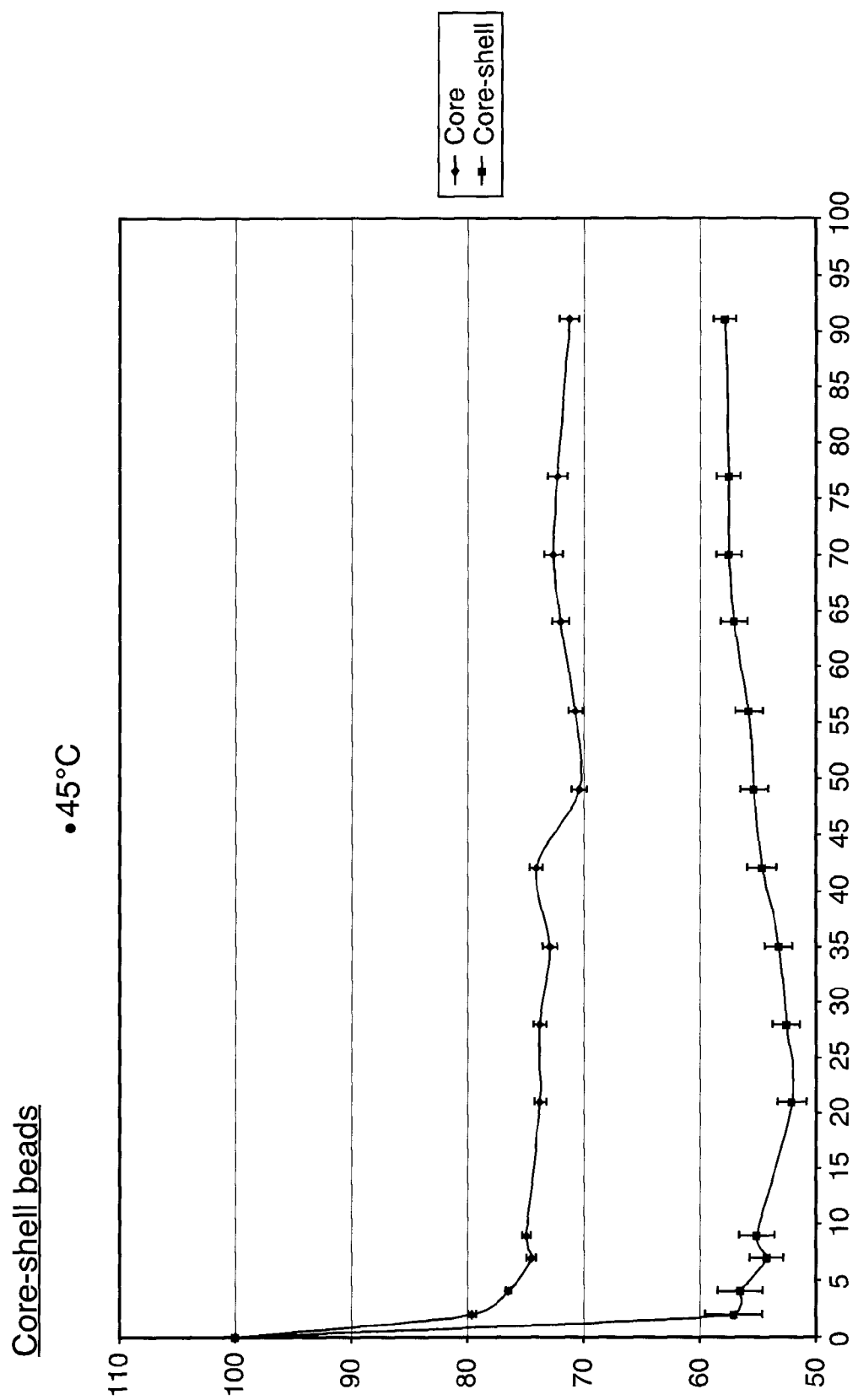
FIG. 11 is a graph showing core shell beads at 45° C.

Referring to FIGS. 8 through 11, core shell polystyrene beads were synthesized by continued addition of styrene monomer to seed beads. Specifically, FIG. 8 shows the size change of the core and core-shell structure of polystyrene beads. FIG. 9 shows the size change of core and core-shell structure of QD barcode beads. FIG. 10 shows core and core-shell QD barcode beads fluorescence intensity over time at about 4° C. FIG. 11 shows the core and core-shell QD barcode beads fluorescence intensity over time at about 45° C.

4. Redox Inhibitor Effect on QD Barcode Beads Brightness

Figure 12:
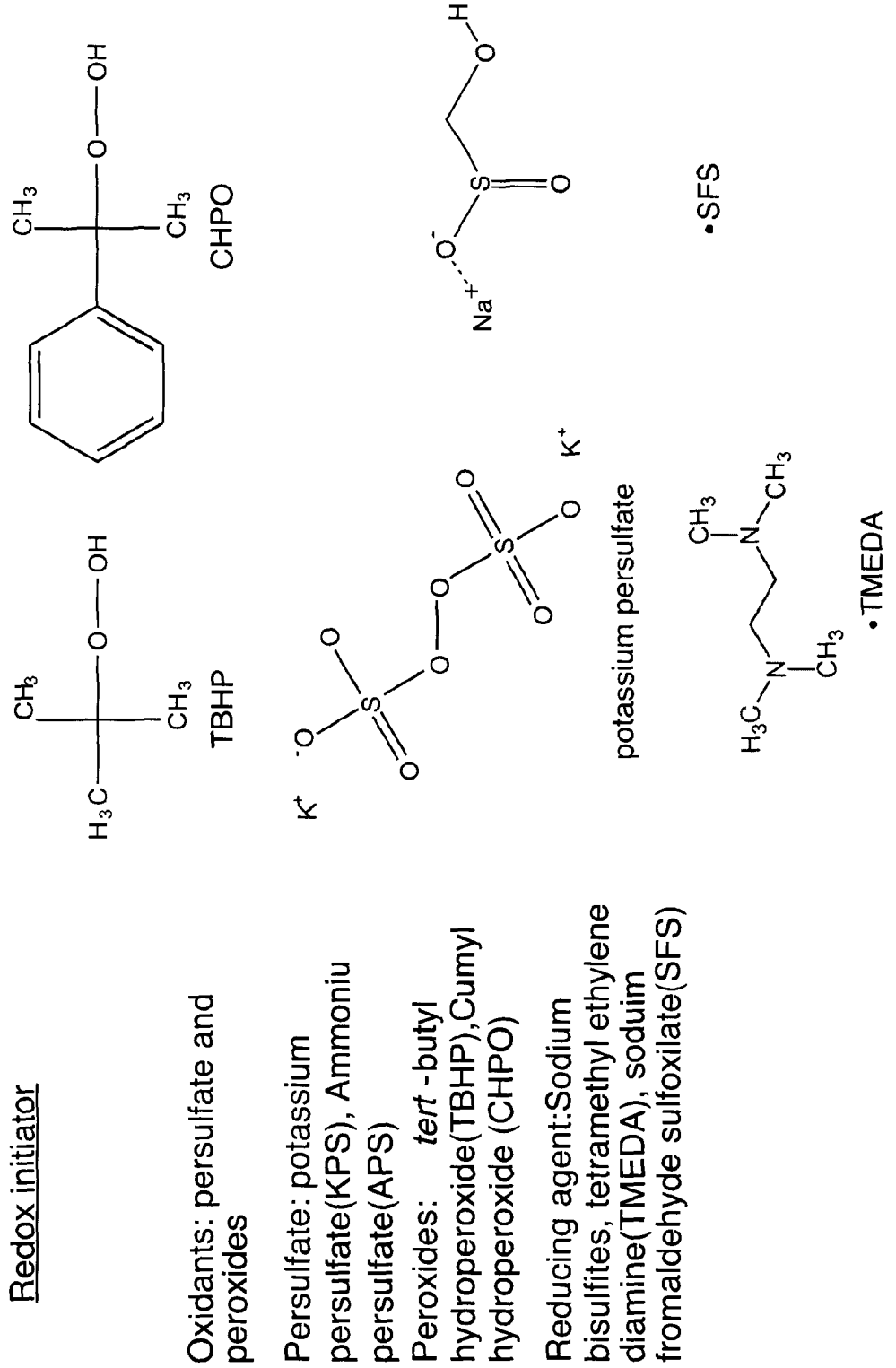
FIG. 12 illustrates example of Redox initiator compounds.
Figure 14:
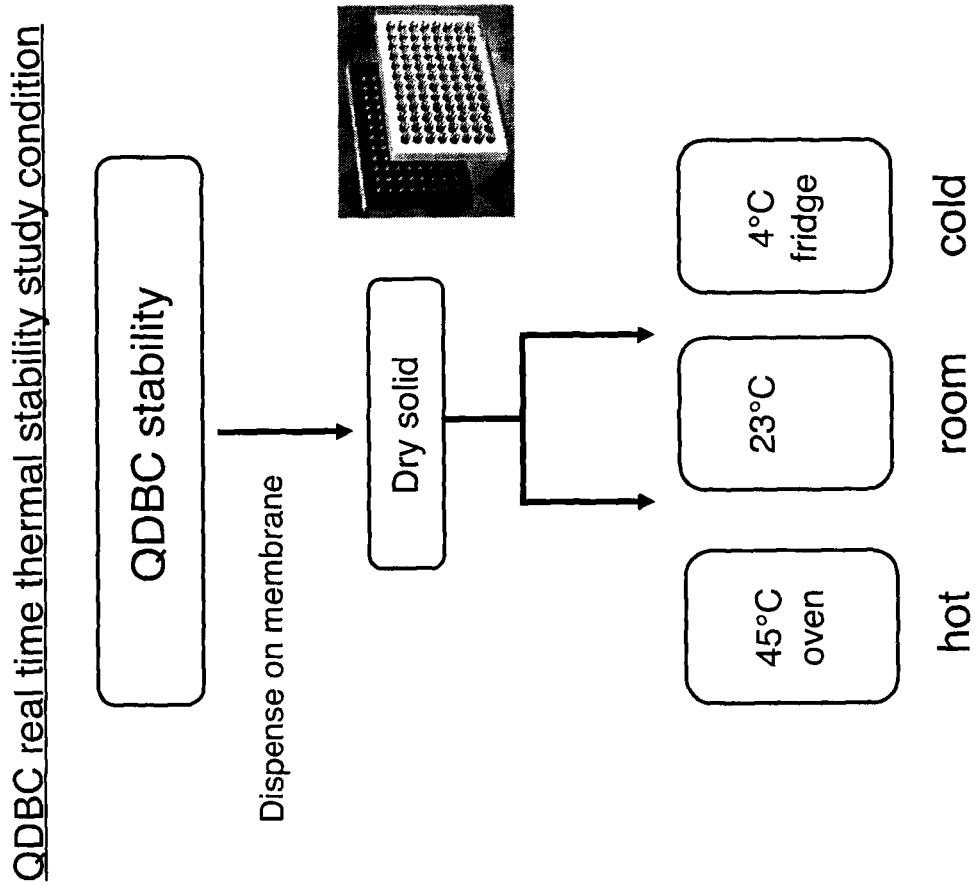
FIG. 14 is a diagrammatic representation of a QDBC real time thermal stability study.
Figure 15:
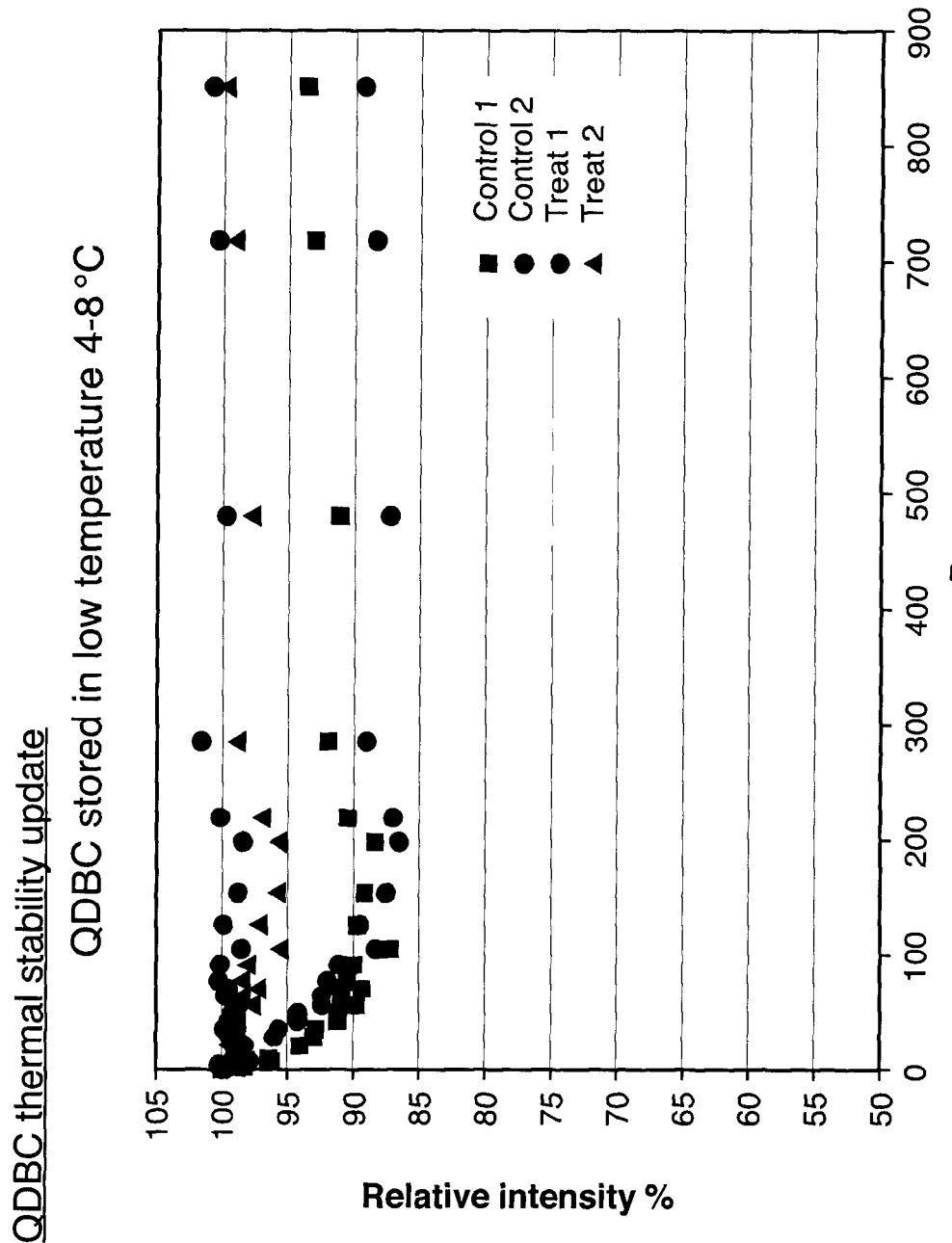
FIG. 15 is a graph showing QDBC thermal stability for QDBC stored at temperatures of about 4-8° C.
Figure 16:
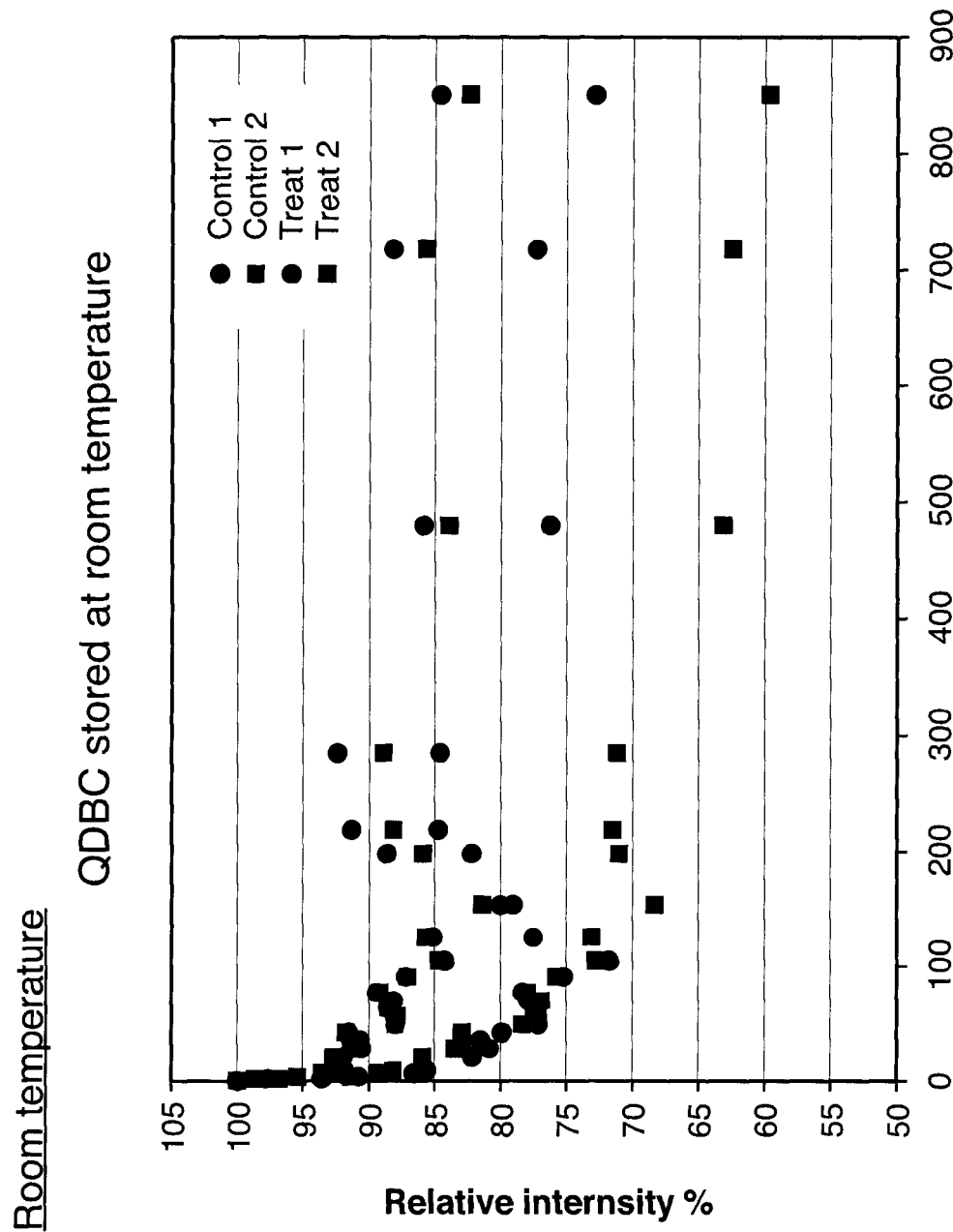
FIG. 16 is a graph showing QDBC stored at room temperature.
Figure 17:
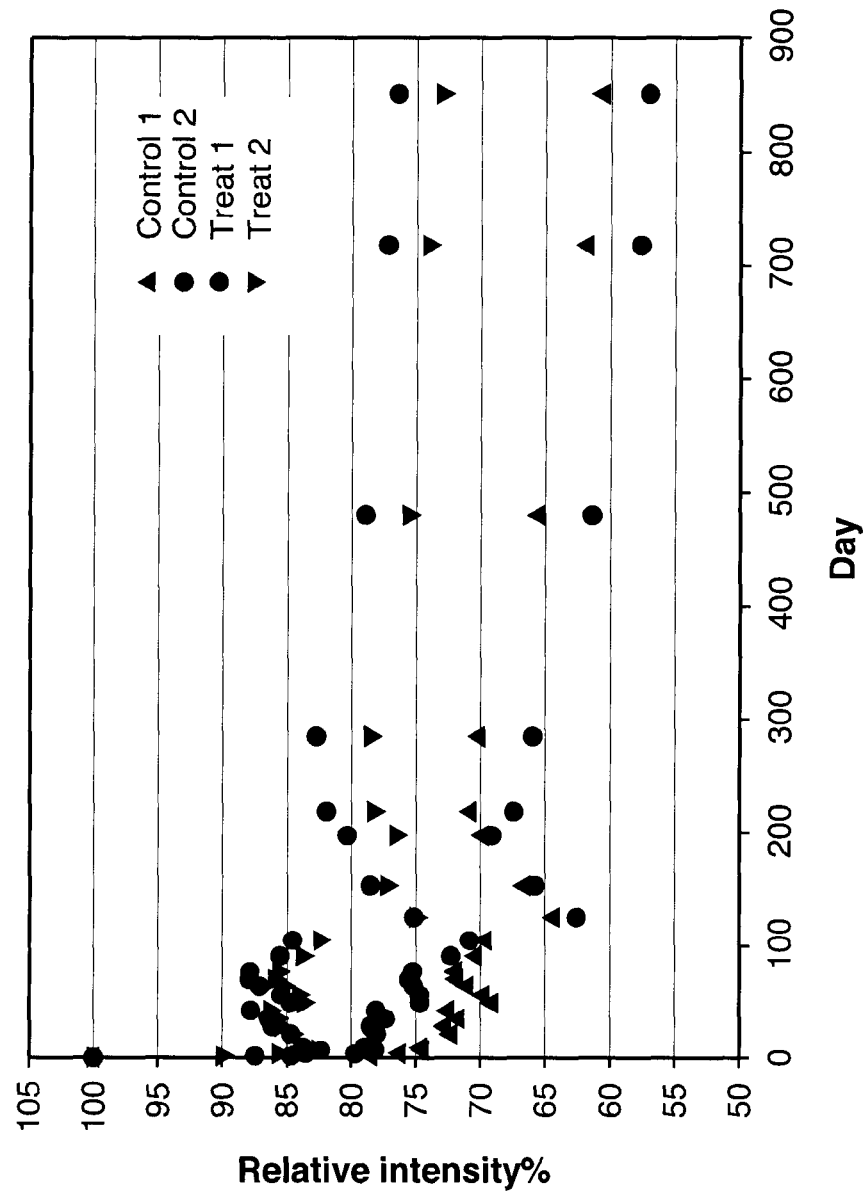
FIG. 17 is a graph showing QDBC stored at temperatures of about 45° C.

Referring to FIG. 12, typically there are two types of oxidants, namely persulfate and peroxides.
  i) Persulfate: potassium persulfate (KPS), Ammonium persulfate (APS)
  ii) Peroxides: tert-butyl hydroperoxide (TBHP), Cumyl hydroperoxide (CHPO).

Reducing agent: Sodium bisulfites, tetramethyl ethylene diamine (TMEDA), sodium formaldehyde sulfoxilate (SFS).

Referring to the Table in FIG. 13, there is illustrated the effect of different redox initiator systems on monomer conversion rate and QD barcode beads intensity

CONCLUSIONS

The core-shell method results in low fluorescence intensity 2.9 times less and poor stability than core barcode beads.

A second monomer can both increase fluorescence intensity (at least 40%) and stability.

Crosslinking results in low intensity (40%), and stability improvement.

A Redox initiator system results in dramatically decreased fluorescence intensity during emulsion polymerization Adding a second monomer in the method may both increase the brightness and stability of QD barcode beads.

Referring to FIGS. 14 through 17, chemical treatment statistically significantly improves the QDBC thermal stability. Furthermore, chemical treatment improves the beads' fluorescence intensity at least about 40%. After chemical treatment, QDBC may keep fluorescence intensity above about 95% over 2 year at low temperature. Furthermore, optimization of storage condition can further increase thermal stability of QDBC*

Regarding the outlook of QDBC for IVD applications, the QDBC fluorescence stability is almost identical to top commercialized organic fluorescence dye beads at low storage temperature, and at high storage temperature, is comparable to top organic dye beads. QDBC is promising for IVD application.

Figure 18:
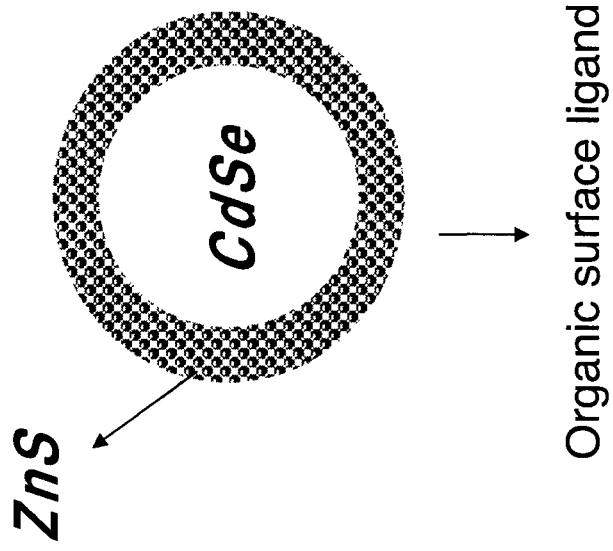
FIG. 18 is a diagrammatic representation of a cadmium selenide/Zinc sulfide quantum dot
Figure 20:
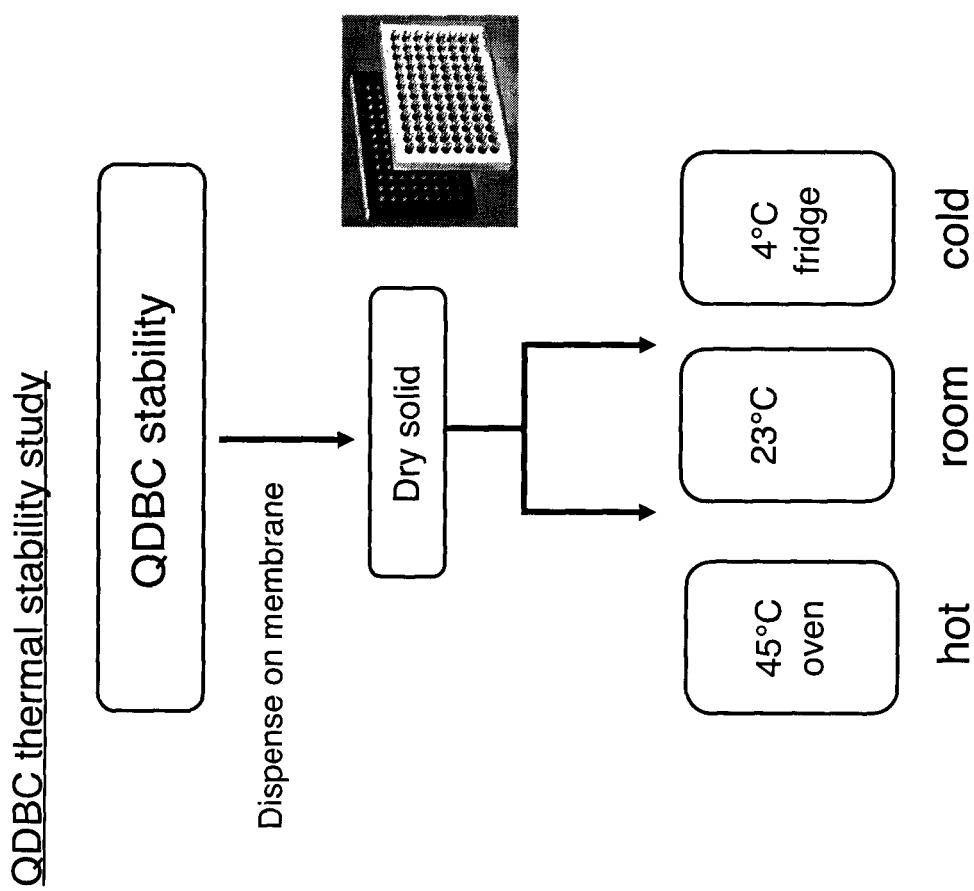
FIG. 20 is a diagrammatic representation of a QDBC thermal stability study.
Figure 21:
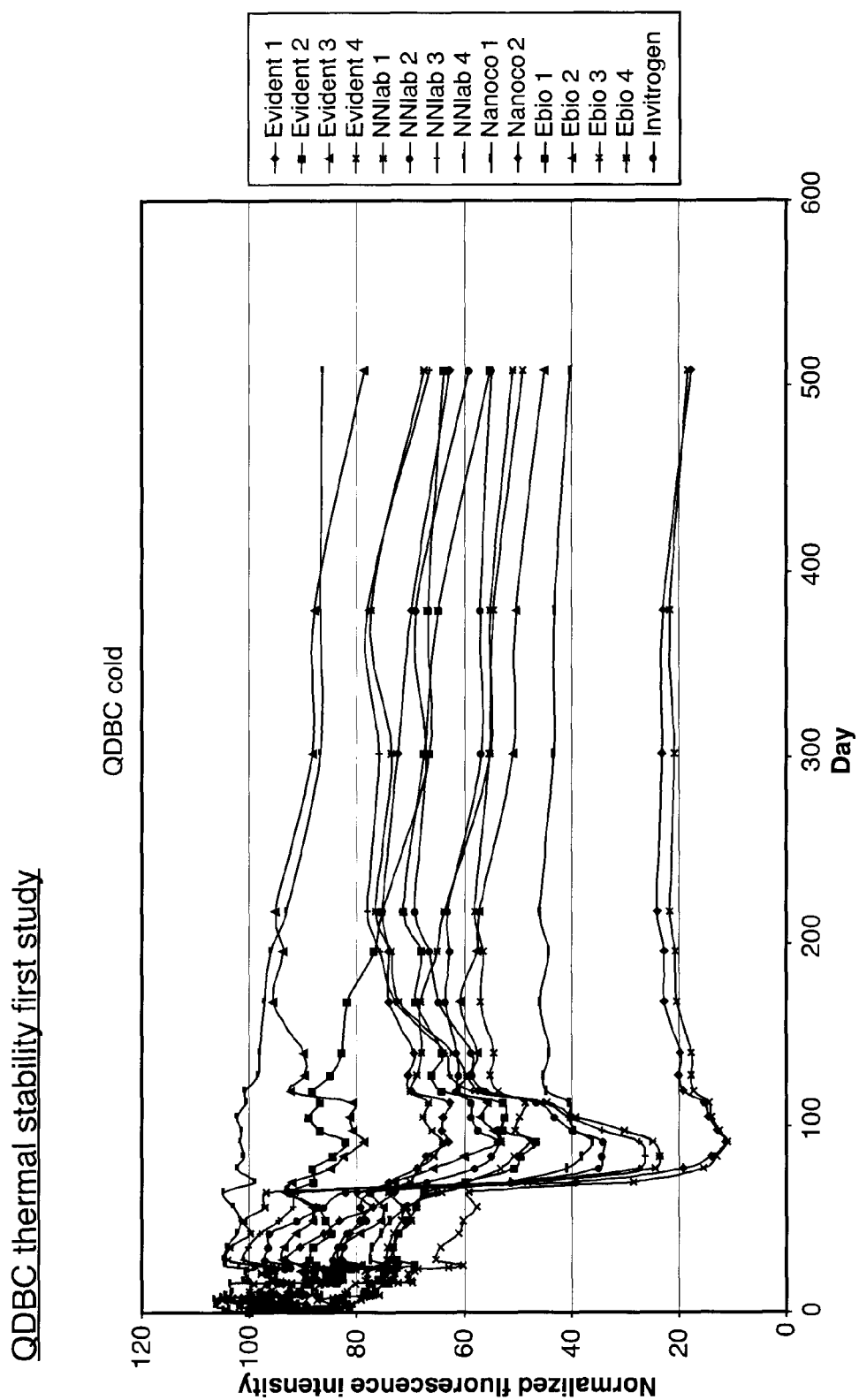
FIG. 21 is a graph illustrating a QDBC thermal stability study at a cold temperature.
Figure 22:
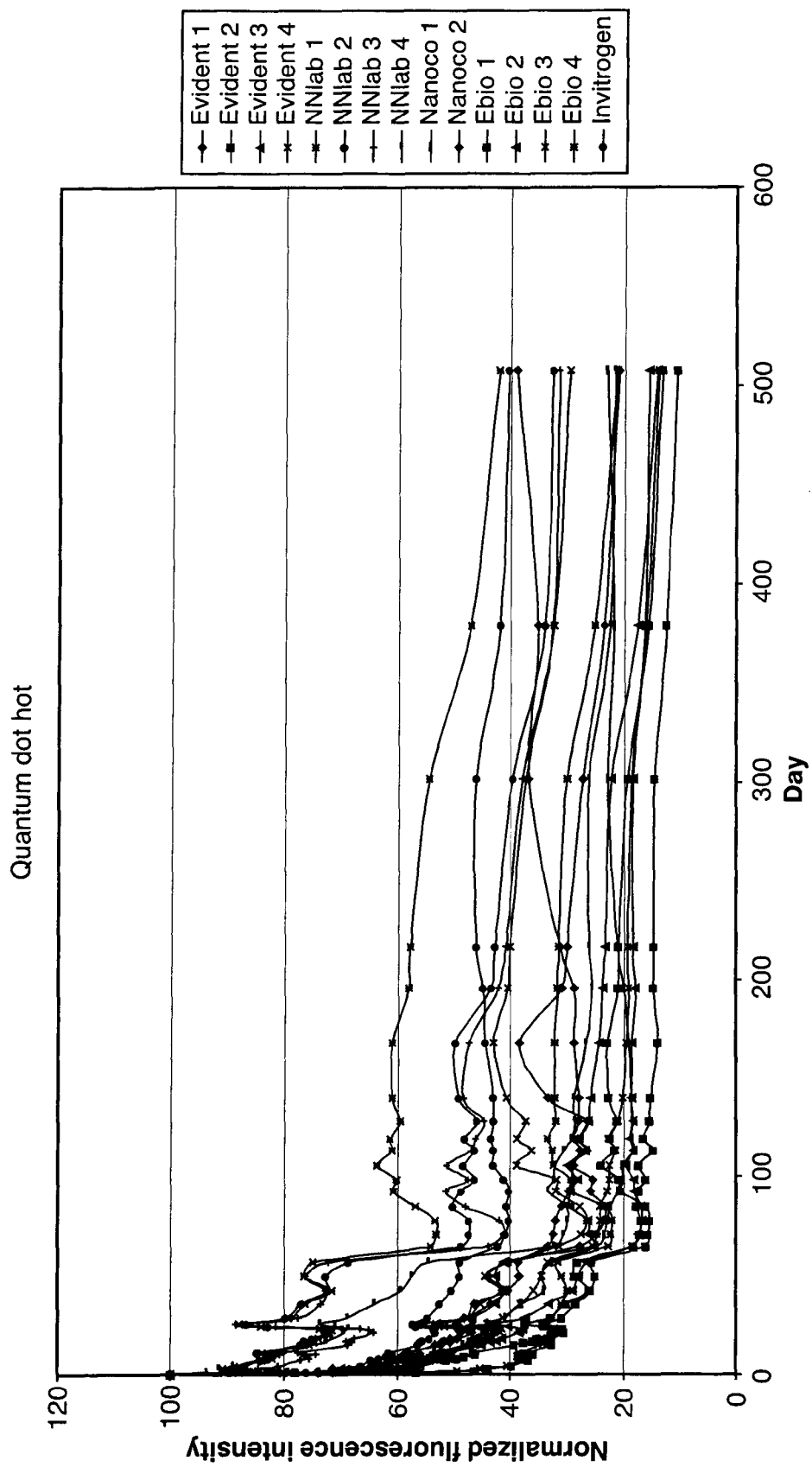
FIG. 22 is a graph illustrating a QDBC thermal stability study at a hot temperature.
Figure 23:
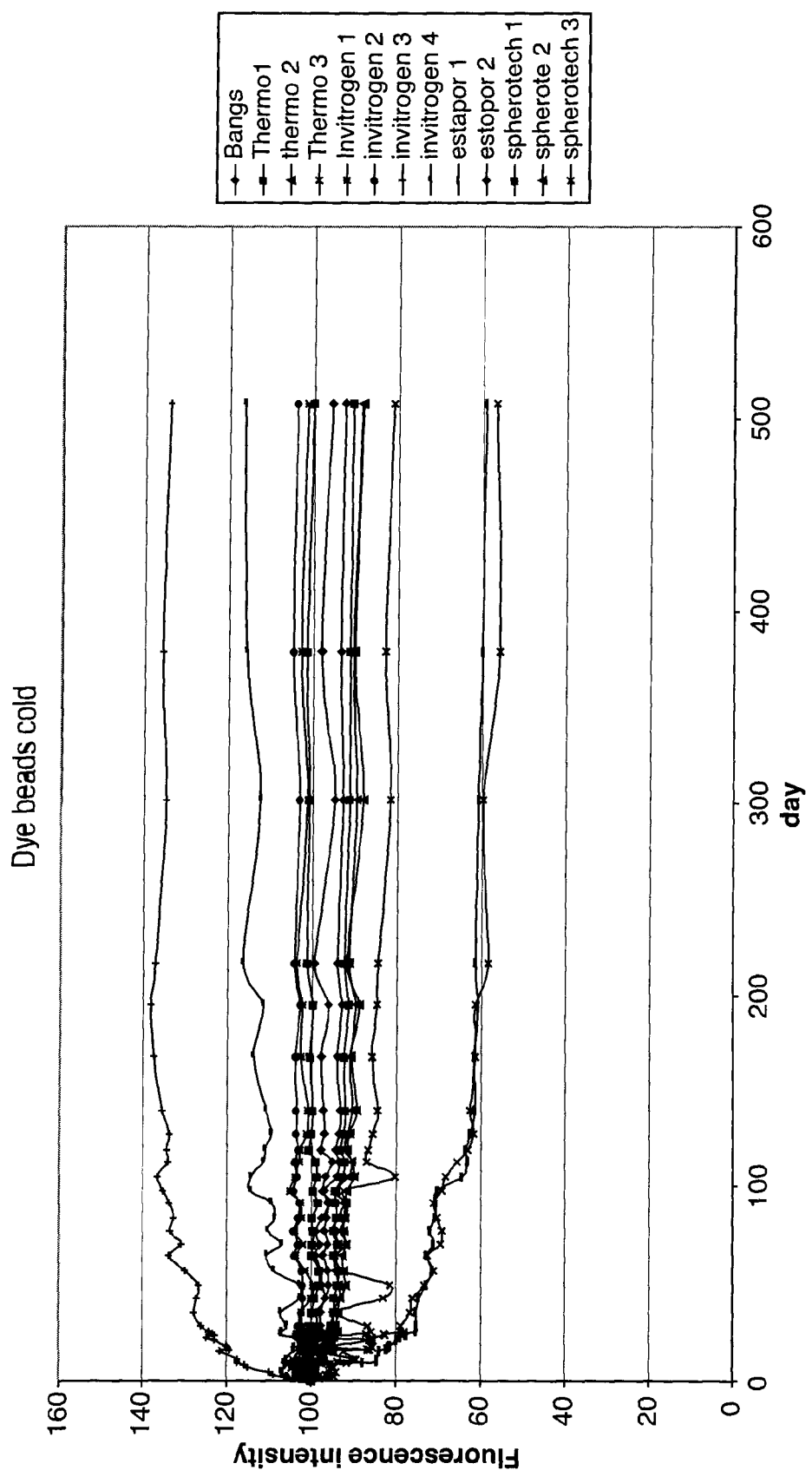
FIG. 23 is a graph illustrating dye beads at a cold temperature.
Figure 24:
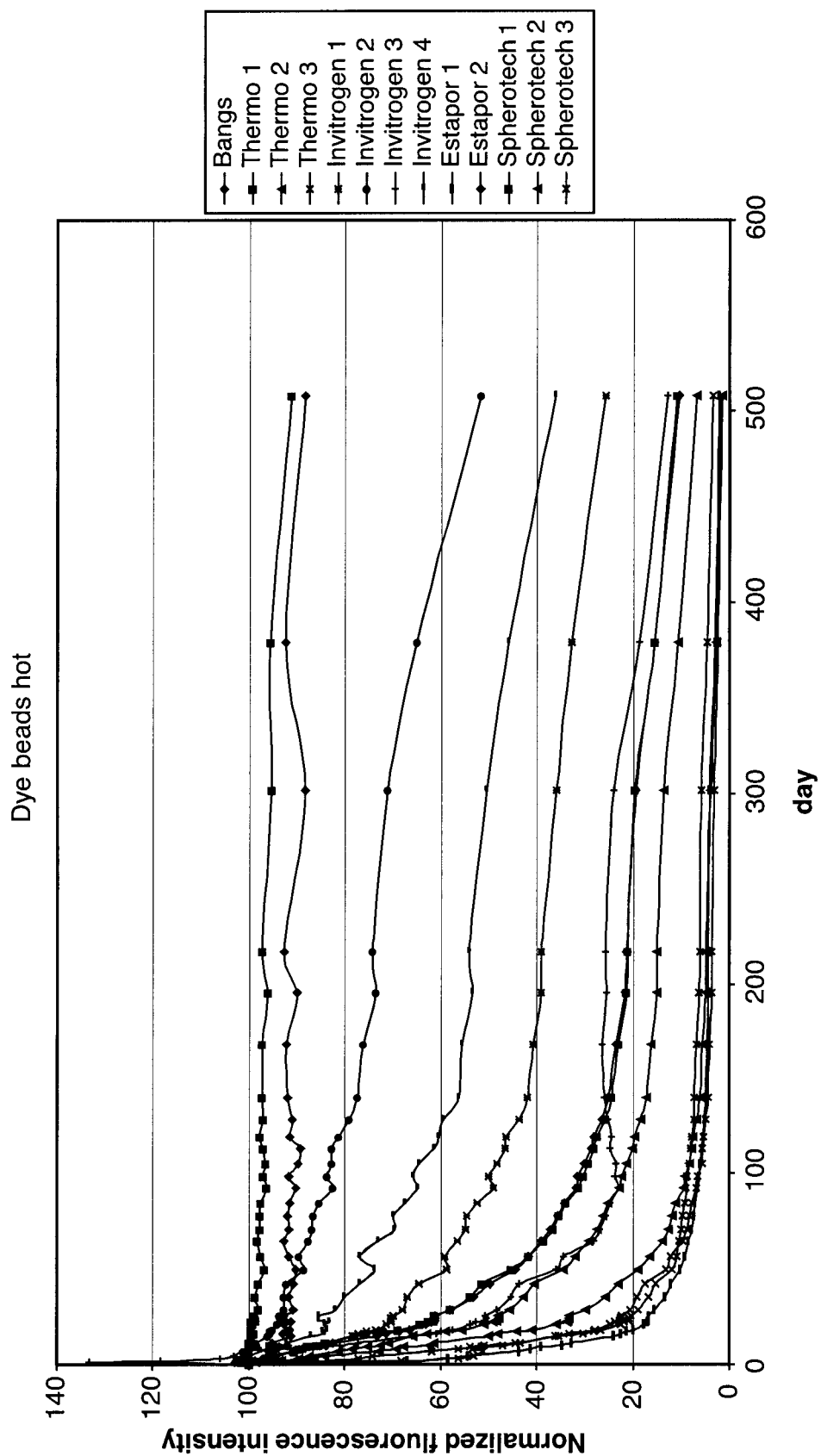
FIG. 24 is a graph illustrating dye beads at a hot temperature.

Assessment of Quantum Dot Barcode Beads (QDBC) for Applications in Quantitative Fluorescence Lateral Flow Product Referring now to FIG. 18, the term "quantum dot" (QD) is intended to refer to cadmium selenide/zinc sulfide (CdSe/ZnS) quantum dots in which a core of CdSe is surrounded by a shell of ZnS, which may be attached to an organic surface ligand.

We attempted to make stable QDBC by adding a second monomer to a) increase the dissolvability of QD in styrene—to increase the fluorescence intensity of QDBC; and b) increase the compatibility of QD in polystyrene matrix to prevent QD segregation from polystyrene. We also optimized storage conditions by a) isolating the QD from oxygen environment; and b) reducing oxidation of the quantum dot.

Figure 25:
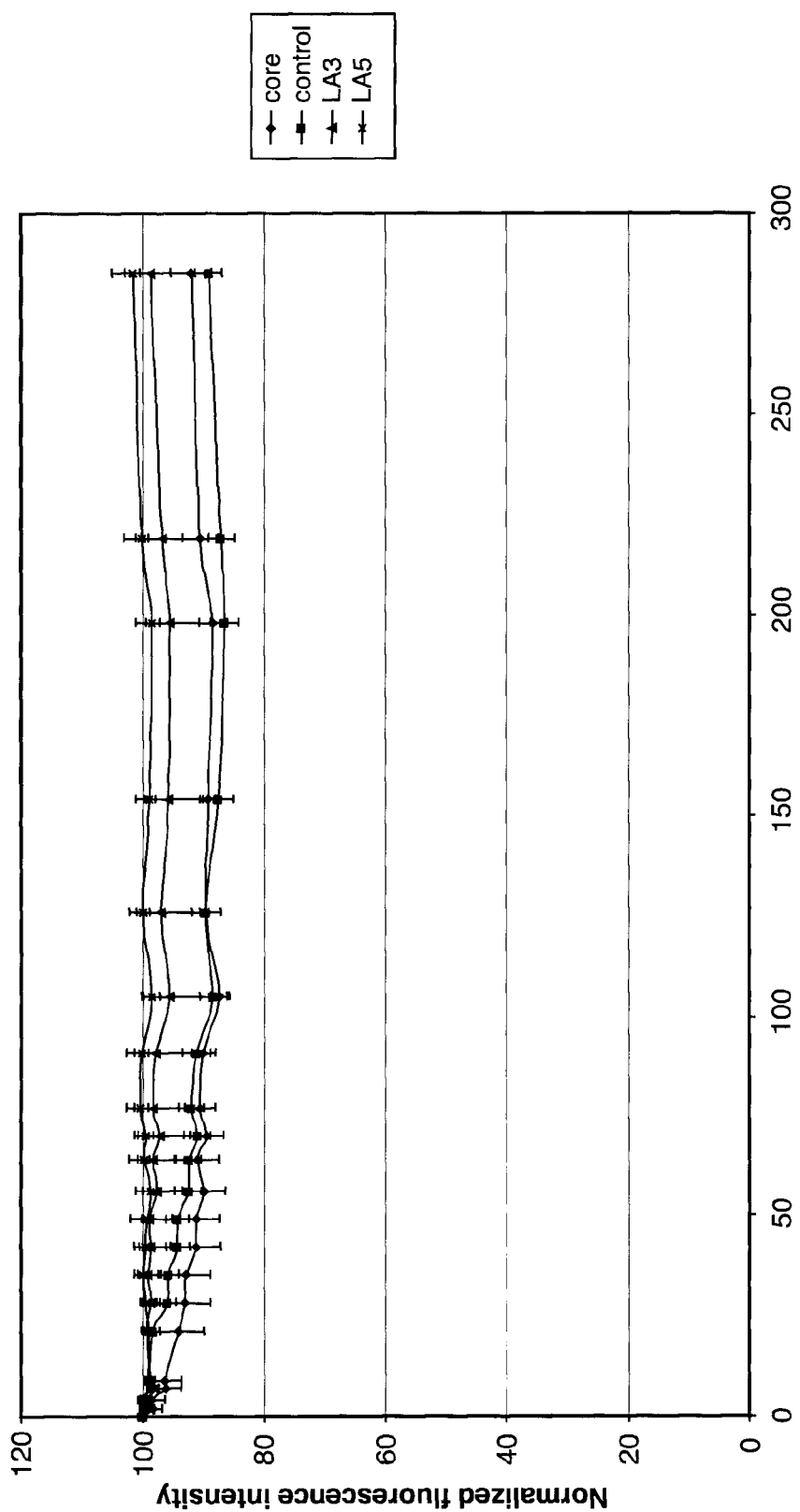
FIG. 25 is a graph showing addition of a second monomer at a cold temperature.
Figure 26:
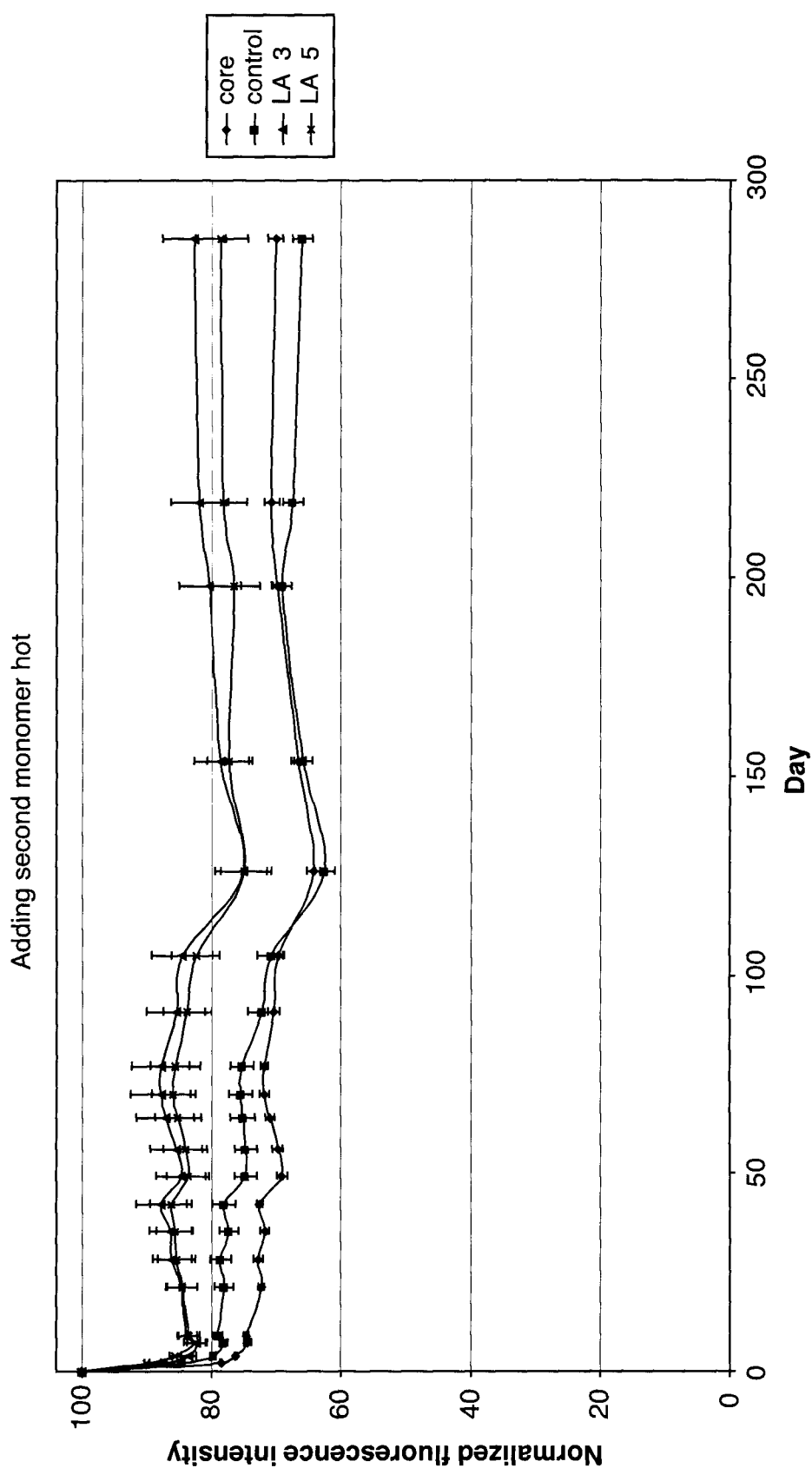
FIG. 26 is a graph showing addition of a second monomer at a hot temperature.
Figure 27A:
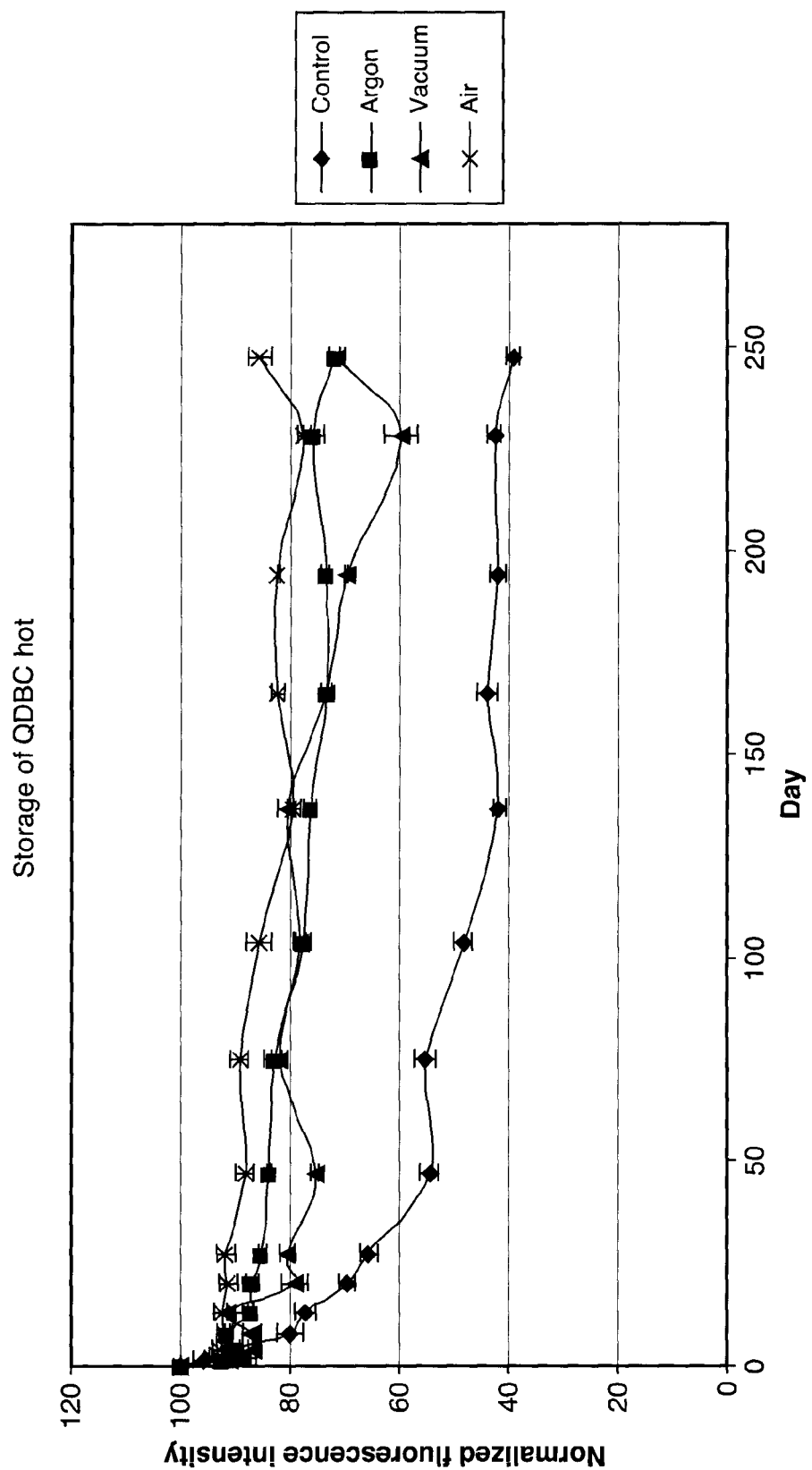
FIG. 27A and FIG. 27B are graphs illustrating optimized storage conditions for the QDBC at a hot temperature and storage dye beads.
Figure 27B:
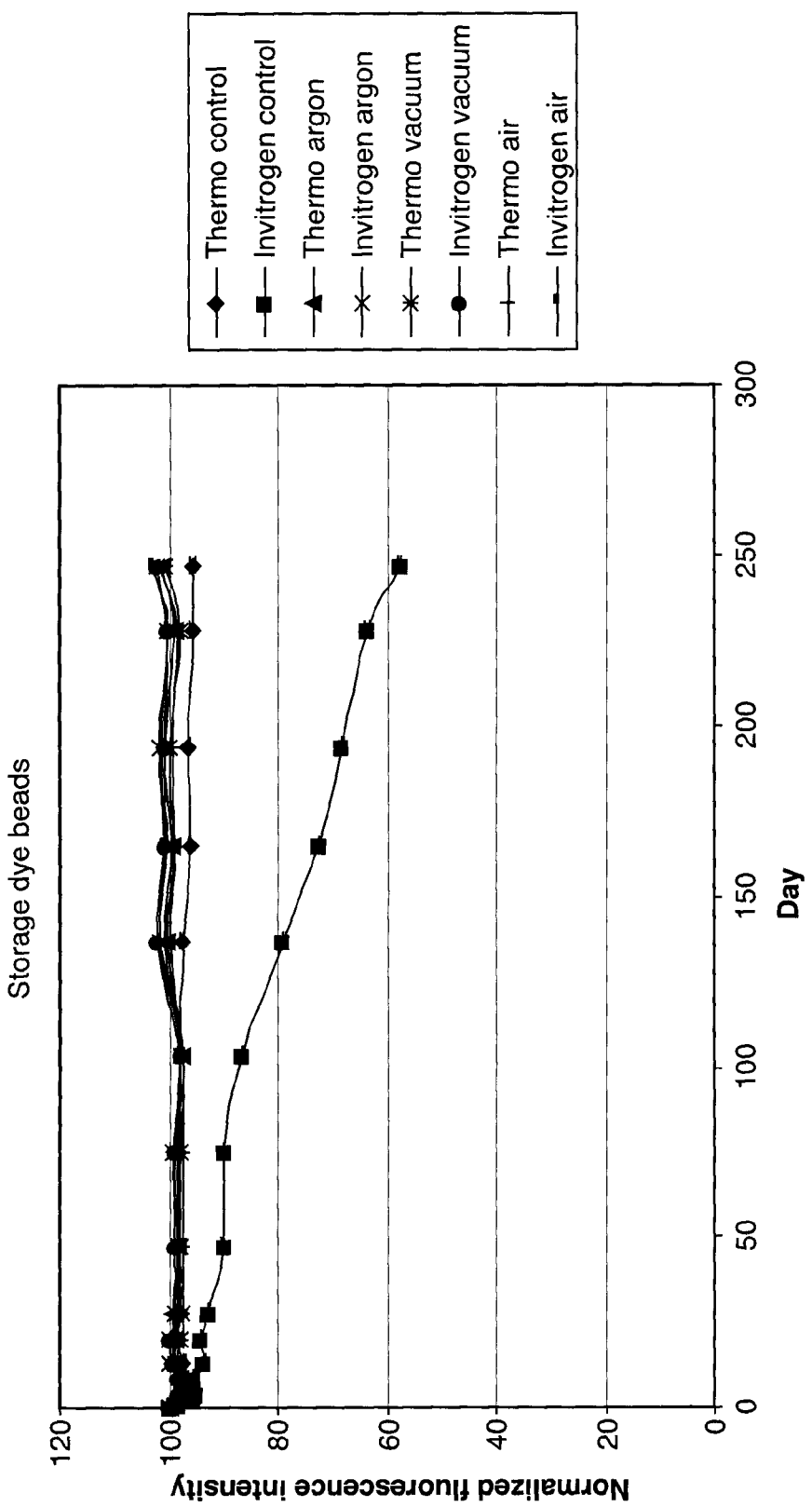

Referring to FIGS. 25 to 27, we conclude that to promote QDBC stability, a) adding a second monomer can both increase fluorescence intensity (at least about 40%) and thermal stability of QDBC; and b) optimization of storage condition can also increase thermal stability of QDBC.

1. Stability: is the ability of the product to retain the performance (sensitivity, specificity and linearity) within specified storage condition throughout its shelf-life.
2. FDA: no regulatory requirements, but requires manufacturers provide stability information, no direct guidance on how to establish such claims
3. There are two accepted standards by IVD industry
   i) EN 13640: European union
   ii) CLSI EP25-A: is a global, nonprofit, standards-developing organization that promotes the development and use of voluntary consensus standards and guidelines within the health care community
4. Shelf-life
5. Define the period of time in which the product remains suitable after being placed into use: control test and recalibration
6. Transport simulation The RoHS (Restriction of Hazardous Substances) established by the European Union calls for the near elimination of 6 chemical substances (lead, cadmium, mercury, hexavalent Chromium, PBBs, PBDEs) used in most electronics and electronic equipment. Each restricted substance has been given a Maximum Concentration Value which determines the maximum amount of each substance that will be allowed in order for that product to be determined to be RoHS Compliant. Cadmium MCV is 0.01%.

Method

The objective was to optimize QDBC beads thermal stability through a chemical modification of synthesis process.

Control: QDBC beads synthesis without chemical modification

Treat: QDBC beads synthesis by adding second monomers during emulsion polymerization Treat 1 vs treat 2: different amount of second monomer.
Fluorescence intensity monitored by M2e plate reader.
Matlab data analysis and statistical analysis by Minitab 16

Although the above description relates to a specific preferred embodiment as presently contemplated by the inventor, it will be understood that the invention in its broad aspect includes mechanical and functional equivalents of the elements described herein.

We claim:

1. A method for stabilizing CdSe/ZnS quantum dots, the method comprising:
    introducing a first monomer into a miniemulsion system comprising the CdSe/ZnS quantum dots, the first monomer being divinylbenzene (DVB); and
    adding a second monomer to the system thereby stabilizing the CdSe/ZnS quantum dots; and
    storing the stabilized CdSe/ZnS quantum dots at a low storage temperature.

2. The method, according to claim 1, in which the second monomer is lauryl acrylate or stearyl methacrylate.

3. The method, according to claim 1, further includes reducing fluorescence quenching by adding a redox initiator system, after addition of the second monomer, at a low temperature so as to increase the brightness of the quantum dots.

4. The method, according to claim 3, in which the redox initiator system is potassium persulfate/sodium bisulfite ($KPS/NaHSO_3$) and ammonium persulfate/tetramethyl ethylene diamine (APS/TMEDA).

5. The method, according to claim 3, in which the low temperature is about 4° C.

6. A method of increasing the brightness of CdSe/ZnS quantum dots, the method comprising:
    adding a redox initiator system to a miniemulsion system comprising the CdSe/ZnS quantum dots stored at a low storage temperature, which includes a first monomer being divinylbenzene (DVB) and a second monomer, at a low temperature to reduce fluorescence quenching, thereby increasing the brightness of the CdSe/ZnS quantum dots.

7. The method, according to claim 6, in which the second monomer is lauryl acrylate or stearyl methacrylate.

8. The method, according to claim 6, in which the redox initiator system is potassium persulfate/sodium bisulfite ($KPS/NaHSO_3$) and ammonium persulfate/tetramethyl ethylene diamine (APS/TMEDA).

9. The method, according to claim 6, in which the low temperature is about 4° C.

* * * * *